US00PP12351P2

(12) United States Plant Patent
Friday

(10) Patent No.: US PP12,351 P2
(45) Date of Patent: Jan. 15, 2002

(54) PEACH TREE NAMED 'P. F. 12-B'

(76) Inventor: Paul Jan Friday, P.O. Box 850, Coloma, MI (US) 49038

( * ) Notice: Subject to any disclaimer, the term of this patent is extended or adjusted under 35 U.S.C. 154(b) by 0 days.

(21) Appl. No.: 09/177,590

(22) Filed: Oct. 22, 1998

(51) Int. Cl.[7] ..... A01H 5/00
(52) U.S. Cl. ..... Plt./198
(58) Field of Search ..... Plt./199, 198

(56) References Cited

U.S. PATENT DOCUMENTS

PP9,939 P * 7/1997 Friday ..... Plt./198
PP10,549 P * 8/1998 Bjorge et al. ..... Plt./198

* cited by examiner

*Primary Examiner*—Howard J. Locker
*Assistant Examiner*—Wendy A. Baker

(57) ABSTRACT

A new and distinct variety of peach *Prunus persica*, tree having the following unique combination of desirable features:

1. The new and distinct variety of peach is of moderate spreading growth and a regular and productive producer of large highly-colored peaches.
2. Producing a very firm fruit having a resilient flesh texture.
3. Blossoms are non-showy when in full bloom.
4. A substantially spherical fruit with an attractive red skin coloring over most of the surface.
5. Early to mid-season maturing fruit of good taste.
6. A peach of good storage and shelf life.

1 Drawing Sheet

ORIGIN OF VARIETY

The new peach tree (*Prunus persica*) (hereinafter referred to as the 'P.F. 12-B' peach tree) was originated by Paul Friday in the experimental orchard, which is maintained for the purpose of breeding peach trees, at Paul Friday Farms Inc., located in Coloma, Mich. Coloma is located in the southwest section of Michigan.

In an ongoing mass selection breeding program, superior seedlings of unrecorded parentage are maintained as seed sources for the production of seeds which are collected and planted in mass. The seed producing parent trees are maintained solely as proprietary trees for breeding purposes and have not been released from the experimental orchard, where such trees can be evaluated for their adaptability to local and regional growing conditions. Seeds resulting from open pollination of the trees in the experimental orchard are regularly planted in mass to produce new populations of seedlings which are cultured and monitored to maturity. Trees with superior attributes are retained for further observation and testing, and contribute seeds to advancing generations of new populations of seedlings.

The tree of this application, 'P.F. 12-B', was a selection from one such cultivated seedling population, and was based on the numerous superior genetic attributes of this tree which are described in the botanical descriptions to follow. While not exhaustive, the botanical descriptions to follow are believed to represent a resonably complete botanical description of the new peach tree which is sufficiently detailed to distinguish the tree from the most closely related trees within the same market class.

ASEXUAL REPRODUCTION OF THE VARIETY

The new and distinct variety of peach tree was asexually propagated by budding onto 'Bailey' rootstock as performed in the experimental orchard of Paul Friday Farms Inc., located in Coloma, Mich. The so stated propagation demonstrates that such reproduction of the characteristics of the tree are consistent and are established and transmitted through succeeding propagation.

SUMMARY OF THE VARIETY

The new and distinct variety of peach tree is of semi-dwarf, moderate spreading growth and is a regular and productive bearer of large peaches. A distinct characteristic of the 'P.F. 12-B' peach tree is its medium vigor, having very stubby new growth with short internodes. The buds are generally one inch apart on the new growth. The blossoms bloom in mid-season and are characterized by being contracted, or partially spreading, in a ¾-inch diameter during bloom.

The blossoms of the present peach tree at full bloom may be characterized as non-showy. More specifically, the blossoms have radially projecting and angularly spaced five-blossom petals to form a blossom having a diameter of about ¾-inch measured across the blossoms.

The flesh of the fruit of the present peach tree is firm, clear, and void of much fiber; it is yellow.

The skin is smooth, having light down, and is of dark red color over about sixty to ninety percent (60% to 90%) of its surface at maturity. The red color overlays yellow. At maturity, the peach is spherical, having a diameter ranging from 2½ inches to 3¼ inches.

The fruit has a firm flesh and may be described as resilient to the extent that the flesh is yieldable and restorable to its original state when subjected to impact forces which may cause bruising and soft blemishes, which lead to rejection by the buyer in the fresh market in peaches of the commercial varieties lacking this quality. This results in less spoilage and also increases the shelf life.

The fruit matures in the early to mid-part of the growing season, three days after the well-known 'Red Haven' variety in southwestern Michigan.

The fruit as mentioned heretofore is of red color over about 60% to 90% of its surface and has a very attractive appearance.

BRIEF DESCRIPTION OF THE PHOTOGRAPHS

In the accompanying photographic illustrations, the top photograph shows one whole specimen from the stem end, as well as one specimen of fruit bisected at a ninety-degree angle to the plane of the suture with the stone retained in one half. The large size obtainable with this variety is also demonstrated with a ruler showing fruit exceeding three inches in diameter.

The second photograph shows many highly colored specimens on the south side of the tree at different orientations while still attached to the stem. The semi-dwarf characteristics of this variety are also demonstrated by the leaves, stems, and short internodes in this photograph.

DESCRIPTION OF VARIETY

The detailed botanical description of the foliage and fruit of the new variety of peach tree is based upon observations of the specimens grown at Coloma, Mich. with the color terminology, other than the terminology expressed in common terms, in accordance with the Pantone Matching System (PMS) as used internationally to identify printed colors.

Tree:
- *Height.*—Unpruned 12'.
- *Width.*—Unpruned 12'.
- *Size.*—Medium.
- *Vigor.*—Medium vigor, terminal growth of 12" to 18" per year.
- *Density.*—Medium, pruning requirements light.
- *Form.*—Spreading.
- *Production.*—Productive, fruit gets good size left heavy on the tree, thus heavy yields.
- *Bearer.*—Consistent.
- *Disease resistance to bacterial leaf and fruit spot.*—Very good. No unusual susceptibility to diseases common to peach has been observed.

Trunk:
- *Size.*—Small to medium.
- *Surface.*—Smooth to medium shaggy.
- *Color.*—Brownish gray.

Branches:
- *Size.*—Small to medium.
- *Surface.*—Smooth to medium.
- *Lenticels.*—Medium number, the size is small 3/16" to 3/8" in length.
- *Color.*—Grayish brown.

Leaves:
- *Size.*—Small to medium. Average length— 5". Average width — 1".
- *Form.*—Lanceolate— pointed. Apex acute to acuminate. Base attenuate to acute.
- *Thickness.*—Medium.
- *Texture.*—Medium.
- *Margin.*—Serrate.
- *Petiole.*—Medium length— medium thickness.
- *Gland.*—Number varies from 4 to 8. They are oval, very small, located on the base of the leaf and upper portion of petiole.
- *Color.*—Upper surface green (356c). Lower surface dull green (357c).

Flower buds:
- *Size.*—Medium.
- *Length.*—Medium.

Flowers:
- *Blooming period.*—Mid-season.
- *Size.*—Medium, about 3/4" diameter.
- *Pollen.*—Present, self-fertilizing.
- *Color.*—Dark pink.

Fruit:
- *Maturity when described.*—Firm ripe.
- *Average date of first picking.*—In Michigan, August 8.
- *Average date of last picking.*—In Michigan, August 18.
- *Size.*—Large, average diameter 2½" to 3¼".
- *Form.*—Spherical.
- *Suture.*—Very shallow.

Skin:
- *Thickness.*—Medium.
- *Texture.*—Tough, tenacious to skin.
- *Tendency to crack.*—None.
- *Down.*—Light.
- *Color.*—Fruit is very attractive, 60% to 90% blushed, ranging from orange-red (1665u) to purple-red (201c) with a yellow (114c) ground color.

Flesh:
- *Texture.*—Firm — non-melting, absence of fiber.
- *Ripens.*—Relatively even.
- *Flavor.*—Excellent; sweet and good balance of sugar to acidity.
- *Aroma.*—Pleasant.
- *Color.*—Yellow (114c) with negligible red around the pit.

Stone:
- *Type.*—Freestone.
- *Size.*—Average length 1½"; average width 1 1/16".
- *Form.*—Ovid.
- *Base.*—Straight.
- *Apex.*—Pointed.
- *Sides.*—Nearly equal.
- *Surface.*—Furrowed.
- *Color.*—Reddish brown (173u).
- *Tendency of crack.*—Slight, about 2%.

Use: Dessert.

Shipping quality: Excellent.

Keeping quality: Good. Can be kept for up to 3 weeks in deep refrigration.

The tree and its fruits herein described may vary in slight detail as a result of differences in climatic or soil conditions or cultural practices under which the tree may be grown. It is to be understood that the description of the new variety as set forth herein is that of the tree grown under the ecological conditions prevailing at Coloma, Mich.

What is claimed is:

1. A new and distinct variety of peach tree substantially as illustrated and described.

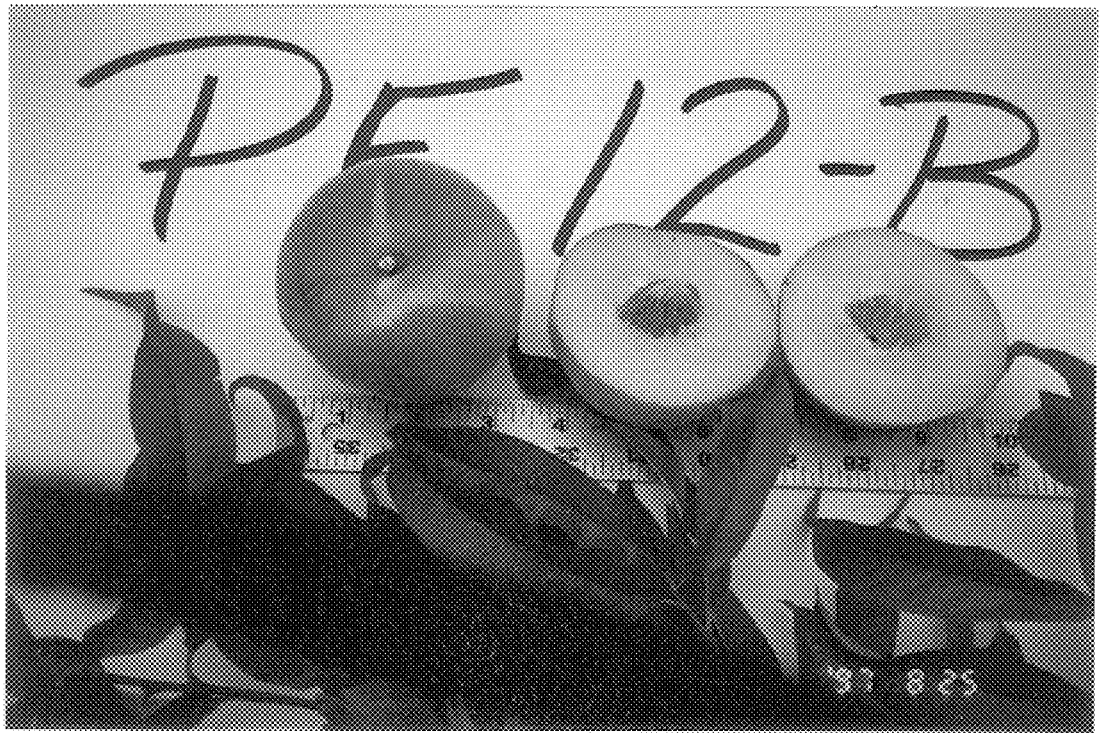
PF12-B
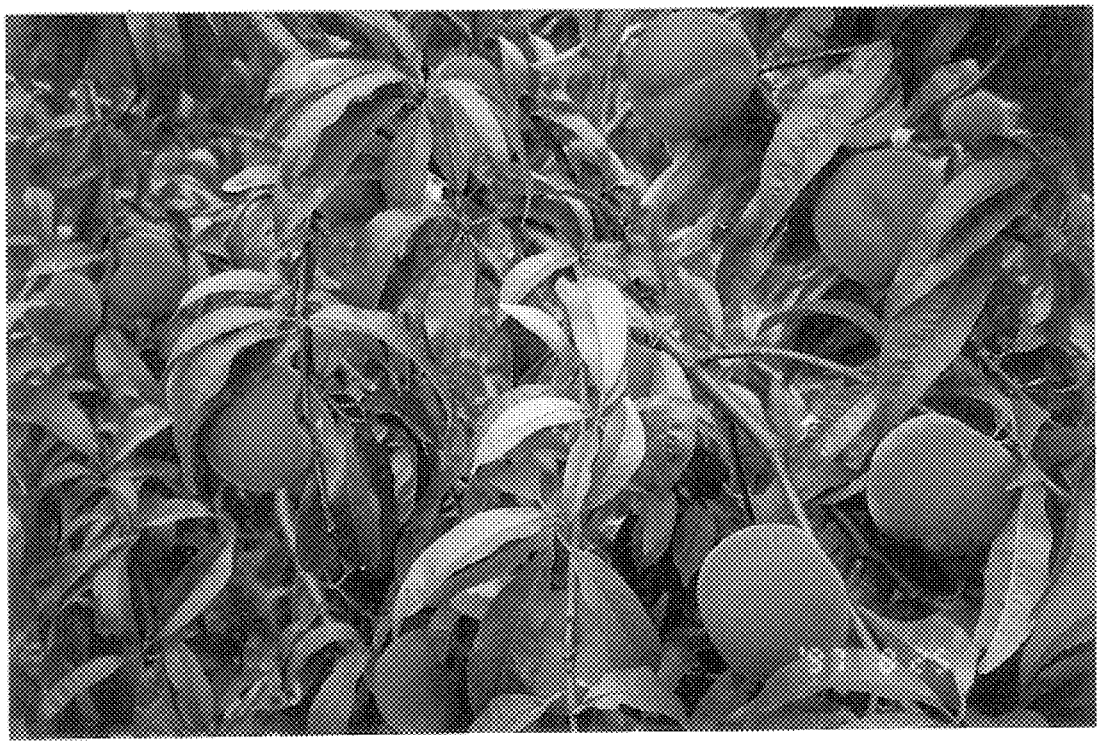

* * * * *